(12) United States Patent
Kojima et al.

(10) Patent No.: US 8,440,422 B2
(45) Date of Patent: May 14, 2013

(54) METHOD FOR MEASURING PHOSPHORIC ACID

(75) Inventors: Ryo Kojima, Koriyama (JP); Yoshiro Sato, Koriyama (JP); Toshihide Miura, Koriyama (JP)

(73) Assignee: Nitto Boseki Co., Ltd., Fukushima-shi (JP)

( * ) Notice: Subject to any disclaimer, the term of this patent is extended or adjusted under 35 U.S.C. 154(b) by 268 days.

(21) Appl. No.: 12/275,635

(22) Filed: Nov. 21, 2008

(65) Prior Publication Data

US 2009/0136978 A1    May 28, 2009

(30) Foreign Application Priority Data

Nov. 22, 2007   (JP) ................. 2007-302495

(51) Int. Cl.
*C12Q 1/32*   (2006.01)
(52) U.S. Cl.
USPC ........................................................... 435/26
(58) Field of Classification Search .................. 435/26, 435/15, 25
See application file for complete search history.

(56) References Cited

FOREIGN PATENT DOCUMENTS

| EP | 0 639 646 B1 | 5/1998 |
|---|---|---|
| EP | 1378575 | 1/2004 |
| EP | 1767931 | 3/2007 |
| JP | 04/349898 | * 12/1992 |
| JP | 4-349898 | 12/1992 |
| JP | 2003-169697 | * 6/2003 |
| JP | 2007-3265 | 1/2007 |
| WO | WO 92/21776 | * 10/1992 |
| WO | WO 92/21776 | 12/1992 |

OTHER PUBLICATIONS

European Search Report dated Mar. 23, 2009.
Rinsho Kensaho Teiyo (Kinbara Shuppan); 31st Revised Edition; 1998; pp. 597-598 including 1 Cover Sheet and 1 End Sheet (4 Sheets total.).
Nihon Rinsho; vol. 43; Special Fall Number in 1985; Kohan-i Ketsueki Nyo Kagakukensa Menekigakutekikensa (Wide-ranging Blood and Urine Chemical Examinations Immunological Examinations (First Volume); 1985; pp. 460-463 including 1 Cover Sheet and 1 End Sheet (6 Sheets total.).

* cited by examiner

*Primary Examiner* — Ralph Gitomer
(74) *Attorney, Agent, or Firm* — Kratz, Quintos & Hanson, LLP

(57) ABSTRACT

In measuring phosphoric acid by the use of an enzyme cycling system using a dehydrogenase together with a thio-NADP, a thio-NAD, a reduced thio-NADP or a reduced thio-NAD as a coenzyme, phosphoric acid is measurable in a wide concentration range from a low concentration to a high concentration by measuring phosphoric acid after previous removal of free phosphoric acid in reagent components for the measurement.

11 Claims, 1 Drawing Sheet

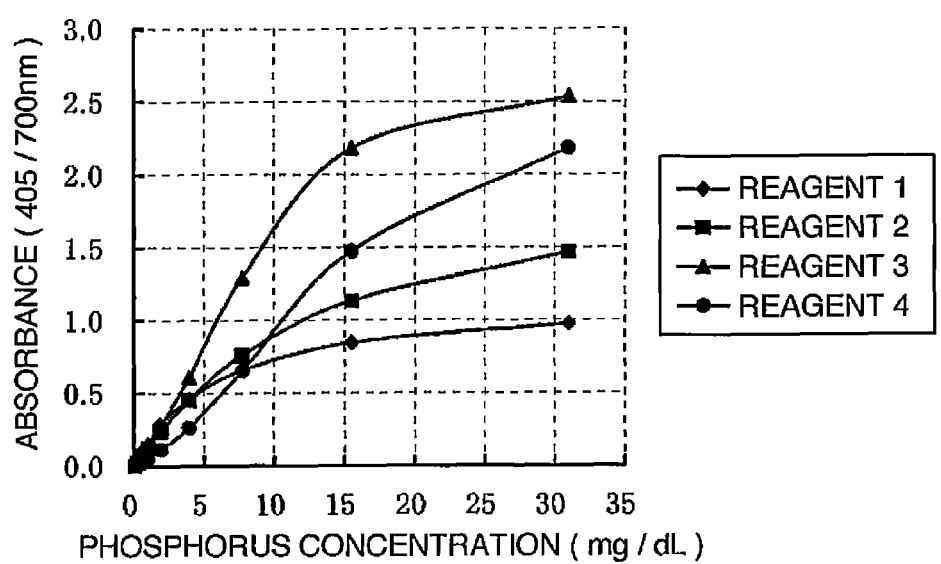

METHOD FOR MEASURING PHOSPHORIC ACID

INCORPORATION BY REFERENCE

The present application claims priority from Japanese application JP 2007-302495 filed on Nov. 22, 2008, the content of which is hereby incorporated by reference into this application.

BACKGROUND OF THE INVENTION

1. Field of the Invention

The present invention relates to a method for measuring phosphoric acid which is useful in clinical biochemical examinations and the like. More particularly, it relates to a method for measuring phosphoric acid by the use of an enzyme cycling system using a dehydrogenase together with a thio-NADP, a thio-NAD, a reduced thio-NADP or a reduced thio-NAD as a coenzyme, which permits measurement of phosphoric acid in a wide concentration range from a low concentration to a high concentration.

2. Description of Related Arts

Phosphoric acid in blood is called "inorganic phosphorus" in clinical examinations and is an important inorganic substance in a living body which is controlled by parathyroid hormone and vitamin D. When the concentration of phosphoric acid in blood is too low, the synthesis of intracellular organic phosphoric acid compounds or cell functions are inhibited. On the other hand, when the phosphoric acid concentration is too high, ectopic calcification or the like is caused. Therefore, various diseases responsible for, for example, incretion or bone metabolism abnormality can be known by analogy by measuring phosphoric acid in blood.

As a method for this measurement, a molybdenum blue method, an enzyme method and the like are known. The molybdenum blue method is a method in which phosphoric acid is measured by adding molybdic acid to phosphate ions in a sample to form a hexavalent phosphomolybdic acid salt (yellow), and adding thereto a reducing agent such as ascorbic acid to form a trivalent phosphomolybdic acid salt (molybdenum blue), followed by colorimetry at 660 to 750 nm (Rinsho Kensaho Teiyo (Kinbara Shuppan), 31th Revised Edition, pp. 597-598 (1998)). The enzyme method, for example, a PNP-XOD-POD method is known as a method for measuring phosphoric acid by carrying out a reaction under milder conditions. The PNP-XOD-POD method is a method in which phosphoric acid is measured by treating phosphate ions in a sample with purine nucleoside phosphorylase (PNP) in the presence of inosine (a substrate) to produce hypoxanthine, making the produced hypoxanthine into uric acid and $H_2O_2$ by the action of xanthine oxidase (XOD), reacting $H_2O_2$ by the use of Trinder's reagent or the like to cause coloration, followed by colorimetry (Nihon Rinsho, Vol. 43, Special Fall Number in 1985, Kohan-i Ketsueki Nyo Kagakukensa•Menekigakutekikensa (Wide-ranging Blood and Urine Chemical Examinations•Immunological Examinations) (First Volume), p. 460 (1985)).

These methods, however, have a low sensitivity as a method for measuring a low concentration of phosphoric acid. The molybdenum blue method is insufficient in reaction specificity. The PNP-XOD-POD method is disadvantageous, for example, in that it is liable to be affected by reducing substances.

On the other hand, in JP-A-4-349898, phosphoric acid is measured by reacting D-glyceraldehyde 3-phosphate, thio-NAD and NADH with phosphoric acid in a sample. This method is advantageous in that phosphoric acid is measurable with high sensitivity by an enzyme cycling reaction method by utilizing the fact that thio-NAD(P)H and NAD(P)H are measurable in distinction from each other because thio-NAD (P)H has an absorbance near 400 nm and NAD(P)H has an absorbance near 340 nm. This method, however, is disadvantageous for practical purpose in that reagents used in this case are expensive, tend to become unstable when dissolved to give an aqueous solution, and have a low storability.

SUMMARY OF THE INVENTION

In view of the problems described above, the present inventor attempted to measure a low concentration of phosphoric acid by the use of an enzyme cycling system using thio-NAD, reduced NAD and a dehydrogenase, and found the following problem: since blank value tends to become high, the measurement is impossible or the range of measurable concentrations becomes narrow. The present invention has been accomplished by solving such a problem.

An object of the present invention is to provide a method for measuring phosphoric acid which reduces reagent blank value, permits measurement of a low concentration of phosphoric acid which is characteristic of an enzyme cycling method, also permits measurement of a high concentration of phosphoric acid, and thus permits measurement of phosphoric acid in a wide concentration range which has been impossible.

The present invention relates to the following items (1) to (22).

(1) A method for measuring phosphoric acid in a test sample by subjecting the phosphoric acid in the test sample to one or more enzyme reactions including an enzyme reaction using a dehydrogenase as the final enzyme reaction; carrying out the enzyme cycling reaction shown in the following reaction scheme (I):

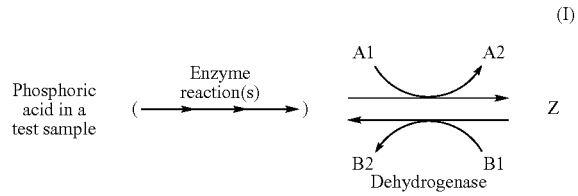

wherein A1 is a thio-NADP, a thio-NAD, an NADP or an NAD, A2 is a reduced product of A1, B1 is a reduced NADP or a reduced NAD in the case of A1 being the thio-NADP or the thio-NAD and is a reduced thio-NADP or a reduced thio-NAD in the case of A1 being the NADP or the NAD, and B2 is an oxidized product of B1, as the enzyme reaction using a dehydrogenase, to form a product Z; and measuring the amount of A2 or B1 which is varied by this reaction, to measure the phosphoric acid in the test sample, which method is characterized in that before the treatment of the phosphoric acid in the test sample with a reagent for carrying out the above-mentioned one or more enzyme reactions, free phosphoric acid present in the components of the reagent is previously removed.

(2) A measuring method according to the above item (1), wherein as a method for previously removing the free phosphoric acid, a method of removing the free phosphoric acid by a physical means using column chromatography or dialysis, or a method of enzymatically removing the free phosphoric acid is practiced.

(3) A measuring method according to the above item (2), wherein as the method of enzymatically removing the free phosphoric acid, a method is practiced in which free phosphoric acid in components of the reagent which are other than the coenzymes for carrying out the enzyme cycling reaction in the above item (1) and are for carrying out the one or more enzyme reactions in the above item (1), is removed by producing a product Z by subjecting the free phosphoric acid in the reagent components other than the coenzymes for carrying out the enzyme cycling reaction in the above item (1) to one or more enzyme reactions including, as the final reaction, the enzyme reaction using a dehydrogenase shown in the reaction scheme (II) shown below, by the use of the reagent components other than the coenzymes for carrying out the enzyme cycling reaction in the above item (1) which are for carrying out the one or more enzyme reactions in the above item (1), and a coenzyme C1 other than the above-mentioned coenzymes which is for carrying out the enzyme reaction using a dehydrogenase shown in the following reaction scheme (II):

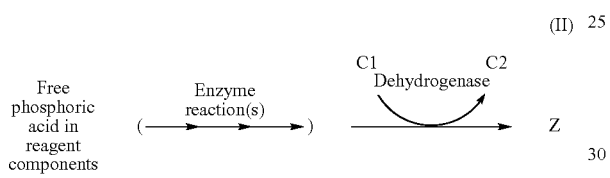

(II)

wherein C1 is a thio-NADP, a thio-NAD, an NADP or an NAD independently of A1 and B1, and C2 is a reduced product of C1, as the final enzyme reaction using a dehydrogenase.

(4) A measuring method according to the above item (3), wherein the reagent components other than the coenzymes for carrying out the enzyme cycling reaction in the above item (1) which are for carrying out the one or more enzyme reactions in the above item (1) are mixed with the coenzyme C1 to put the free phosphoric acid in the reagent components together, and the resulting mixture of the reagent components containing the free phosphoric acid put together was heated to carry out the one or more enzyme reactions including, as the final reaction, the enzyme reaction using a dehydrogenase shown in the reaction scheme (II), whereby the free phosphoric acid is removed.

(5) A measuring method according to any one of the above items (2) to (4), wherein the enzyme reaction using a dehydrogenase shown in the reaction scheme (II) is carried out at pH 4.0 to 7.5 and the thus produced reduction product C2 of the thio-NADP, the thio-NAD, the NADP or the NAD is decomposed by degrees.

(6) A measuring method according to any one of the above items (2) to (5), wherein an enzyme system in which the amount of the product Z is reduced by degrees is also made present at the time of the enzyme reaction using a dehydrogenase shown in the reaction scheme (II).

(7) A measuring method according to any one of the above items (1) to (6), wherein the single enzyme reaction, i.e., the enzyme reaction using a dehydrogenase as the final enzyme reaction is represented by the following scheme:

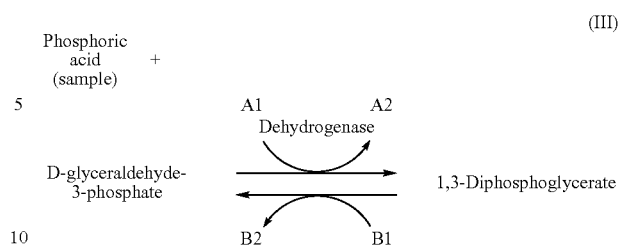

wherein the dehydrogenase is D-glyceraldehyde-3-phosphate dehydrogenase, and A1, A2, B1 and B2 are as defined above.

(8) A measuring method according to the above item (7), wherein the free phosphoric acid present in the reagent components is removed by subjecting the free phosphoric acid in the reagent components, i.e., D-glyceraldehyde 3-phosphate, D-glyceraldehyde-3-phosphate dehydrogenase and a thio-NADP, a thio-NAD, an NADP or an NAD to an enzyme reaction represented by the following scheme (IV):

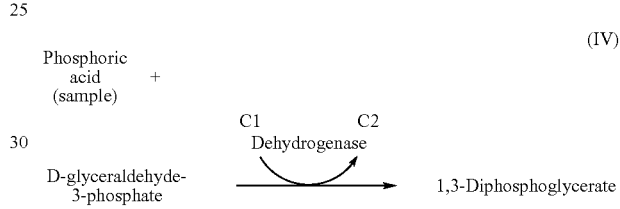

wherein the dehydrogenase is D-glyceraldehyde-3-phosphate dehydrogenase, and C1 and C2 are as defined above, by using the reagent components.

(9) A measuring method according to the above item (8), wherein in removing the free phosphoric acid, an enzyme reaction represented by the following reaction scheme (V):

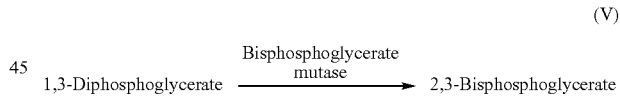

is carried out by adding biphosphoglycerate mutase to the reagent components as an enzyme for reducing the amount of the product 1,3-diphosphoglycerate.

(10) A measuring method according to any one of the above items (1) to (6), wherein the two or more enzyme reactions including an enzyme reaction using a dehydrogenase as the final enzyme reaction are represented by the following scheme (VI):

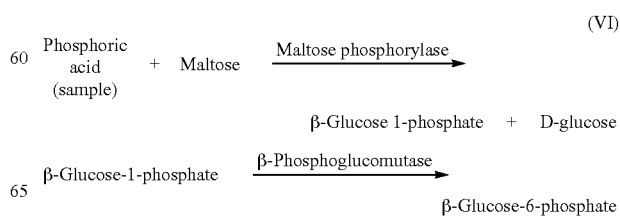

-continued

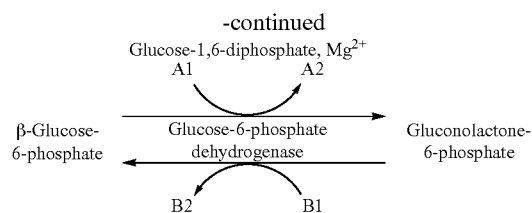

wherein A1, A2, B1 and B2 are as defined above.

(11) A measuring method according to the above item (10), wherein the free phosphoric acid present in the reagent components is removed by subjecting the free phosphoric acid in the reagent components, i.e., maltose, maltose phosphorylase, β-phosphoglucomutase, glucose-6-phosphate dehydrogenase and a thio-NADP, a thio-NAD, an NADP or an NAD to enzyme reactions represented by the following scheme (VII):

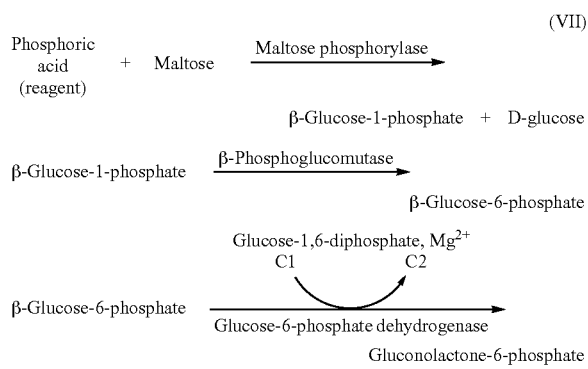

wherein C1 and C2 are as defined above, by using the reagent components.

(12) A measuring method according to the above item (11), wherein in removing the free phosphoric acid, an enzyme reaction represented by the following reaction scheme (VIII):

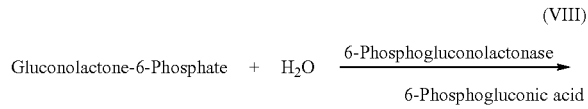

is carried out by adding 6-phosphogluconolactonase to the reagent components as an enzyme for reducing the amount of the product gluconolactone 6-phosphate.

(13) A measuring method according to any one of the above items (1) to (12), wherein the NADP is selected from the group consisting of nicotinamide adenine dinucleotide phosphate (NADP), acetylpyridine adenine dinucleotide phosphate (acetyl-NADP), acetylpyridine hypoxanthine dinucleotide phosphate and nicotinamide hypoxanthine dinucleotide phosphate (deamino-NADP).

(14) A measuring method according to any one of the above items (1) to (12), wherein the NAD is selected from the group consisting of nicotinamide adenine dinucleotide (NAD), acetylpyridine adenine dinucleotide (acetyl-NAD), acetylpyridine hypoxanthine dinucleotide and nicotinamide hypoxanthine dinucleotide (deamino-NAD).

(15) A measuring method according to any one of the above items (1) to (12), wherein the thio-NADP is selected from the group consisting of thionicotinamide adenine dinucleotide phosphate (thio-NADP) and thionicotinamide hypoxanthine dinucleotide phosphate.

(16) A measuring method according to any one of the above items (1) to (12), wherein the thio-NAD is selected from the group consisting of thionicotinamide adenine dinucleotide (thio-NAD) and thionicotinamide hypoxanthine dinucleotide.

(17) A kit for measuring phosphoric acid which is for measuring phosphoric acid in a test sample by subjecting the phosphoric acid in the test sample to one or more enzyme reactions including an enzyme reaction using a dehydrogenase as the final enzyme reaction, and which comprises 1) a reagent for removing free phosphoric acid comprising reagent components other than the coenzymes for carrying out the enzyme cycling reaction in the reaction scheme (I) in the above item (1) which are for carrying out the one or more enzyme reaction in the above item (1), and a coenzyme for carrying out the final enzyme reaction in the reaction scheme (II) in the above item (3); or a reagent freed from free phosphoric acid which is obtained by subjecting said reagent for removing free phosphoric acid to an enzyme reaction, and 2) the coenzymes for carrying out the enzyme cycling reaction in the reaction scheme (I) in the above item (1).

(18) A kit for measuring phosphoric acid in a test sample according to the above item (17), which comprises 1) a reagent for removing free phosphoric acid comprising D-glyceraldehyde 3-phosphate, D-glyceraldehyde-3-phosphate dehydrogenase and a thio-NADP, a thio-NAD, an NADP or an NAD, or a reagent freed from free phosphoric acid which is obtained by subjecting said reagent for removing free phosphoric acid to an enzyme reaction, and 2) a pair of coenzymes comprising a combination of a thio-NADP or a thio-NAD and a reduced NADP or a reduced NAD, or a pair of coenzymes comprising a combination of an NADP or an NAD and a reduced thio-NADP or a reduced thio-NAD.

(19) A kit for measuring phosphoric acid in a test sample according to the above item (17), which comprises 1) a reagent for removing free phosphoric acid comprising maltose, maltose phosphorylase, β-phosphoglucomutase, glucose-6-phosphate dehydrogenase and a thio-NADP, a thio-NAD, an NADP or an NAD, or a reagent freed from free phosphoric acid which is obtained by subjecting said reagent for removing free phosphoric acid to an enzyme reaction, and 2) a pair of coenzymes comprising a combination of a thio-NADP or a thio-NAD and a reduced NADP or a reduced NAD, or a pair of coenzymes comprising a combination of an NADP or an NAD and a reduced thio-NADP or a reduced thio-NAD.

(20) A method for measuring phosphoric acid or maltose in a test sample characterized by adding a reagent for carrying out enzyme reactions using maltose phosphorylase, β-phosphoglucomutase and glucose-6-phosphate dehydrogenase, respectively, to phosphoric acid or maltose in the test sample; adding thereto a pair of coenzymes comprising a combination of a thio-NADP or a thio-NAD and a reduced NADP or a reduced NAD, or a pair of coenzymes comprising a combination of an NADP or an NAD and a reduced thio-NADP or a reduced thio-NAD, as a reagent for carrying out an enzyme reaction using said glucose-6-phosphate dehydrogenase; carrying out, as the final enzyme reaction, the enzyme cycling reaction using said glucose-6-phosphate dehydrogenase and shown in the following scheme (IX):

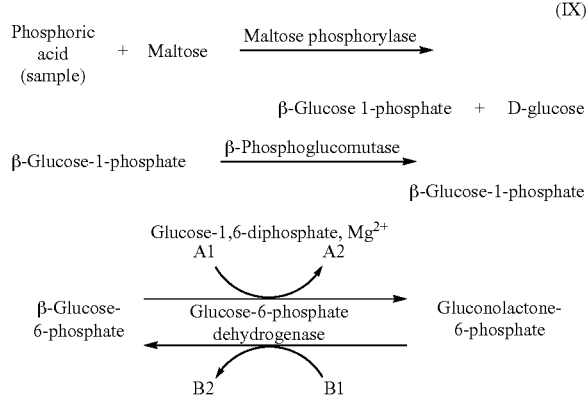

(IX)

wherein A1 is the thio-NADP, the thio-NAD, the NADP or the NAD, A2 is a reduced product of A1, B1 is the reduced NADP or the reduced NAD in the case of A1 being the thio-NADP or the thio-NAD and is the reduced thio-NADP or the reduced thio-NAD in the case of A1 being the NADP or the NAD, and B2 is an oxidized product of B1, to produce gluconolactone 6-phosphate; and measuring the amount of A2 or B1 which is varied by the reaction.

(21) A measuring method according to the above item (20), wherein 6-phosphogluconolactonase is made present in an enzyme system in which the amount of the product gluconolactone 6-phosphate is reduced by degrees.

(22) A method for measuring phosphoric acid in a test sample, or a substrate Y reactive with the phosphoric acid in the presence an enzyme X, which comprises adding a reagent for enabling the enzyme X to undergo an enzyme reaction in the case of the enzyme X being a dehydrogenase, or a reagent capable of permitting two or more enzyme reactions including at least a reaction using the enzyme X as the first reaction and a reaction using a dehydrogenase as the final reaction; adding a pair of coenzymes comprising a combination of a thio-NADP or a thio-NAD and a reduced NADP or a reduced NAD, or a pair of coenzymes comprising a combination of an NADP or an NAD and a reduced thio-NADP or a reduced thio-NAD, as a reagent for carrying out the enzyme reaction using the dehydrogenase; carrying out the enzyme cycling reaction shown in the following reaction scheme (X):

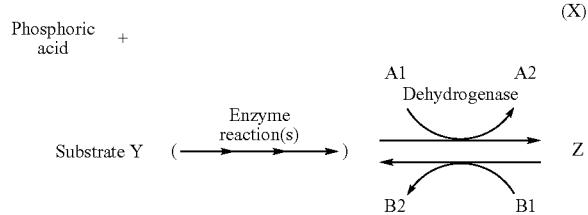

(X)

wherein A1 is the thio-NADP, the thio-NAD, the NADP or the NAD, A2 is a reduced product of A1, B1 is the reduced NADP or the reduced NAD in the case of A1 being the thio-NADP or the thio-NAD and is the reduced thio-NADP or the reduced thio-NAD in the case of A1 being the NADP or the NAD, and B2 is an oxidized product of B1, to produce a product Z; and measuring the amount of A2 or B1 which is varied by the reaction, to measure phosphoric acid, which method is characterized in that an enzyme system in which the amount of the product Z is reduced by degrees is made present.

Employment of any of the measuring methods and kits of the present invention described in the above items (1) to (19) is advantageous in that when phosphoric acid is measured by the use of an enzyme system involving an enzyme cycling reaction using a dehydrogenase and a combination of specific coenzymes, blank value in the measurement is reducible by previously removing phosphoric acid present in components other than the coenzymes in a reagent, so that phosphoric acid is measurable in a wide concentration range from a low concentration to a high concentration.

Adoption of any of the measuring methods of the present invention described in the above items (20) and (21) is advantageous in that when phosphoric acid or maltose is measured by an enzyme cycling reaction using a dehydrogenase and a combination of specific coenzymes, reagents used in this case are inexpensive and they are stable when dissolved to give an aqueous solution, so that a low concentration of phosphoric acid or maltose is accurately measurable by the use of the reagents which are storable for a long period of time. Furthermore, adoption of the measuring method of the present invention described in the above item (22) is advantageous in that when phosphoric acid or a specific substrate for enzyme is measured by the use of an enzyme system involving an enzyme cycling reaction using a dehydrogenase and a combination of specific coenzymes, the rate of the enzyme cycling reaction is controllable by the presence of a system in which the amount of the final product is further reduced by degrees, and hence the concentration of phosphoric acid is measurable in a wide range from a high concentration to a low concentration.

BRIEF DESCRIPTION OF THE DRAWINGS

FIG. 1 shows the absorbance change in the phosphoric acid concentration measurement shown in Table 2.

DETAILED DESCRIPTION OF THE INVENTION

The substance to be measured in each of the measuring methods of the present invention described in the above items (1) to (16) is phosphoric acid. When an enzyme system in which phosphoric acid is released or produced is present, the enzyme activity in the enzyme system and a substrate for the enzyme are measurable by measuring phosphoric acid intermediately produced.

The phosphoric acid in the present invention may be inorganic phosphoric acid or its ionized product and includes, for example, $H_3PO_4$, $H_2PO_4^-$ ions, $HPO_4^{2-}$ ions and $PO_4^{3-}$ ions. Each of these ionized products may be a salt such as Na salt, K salt or ammonium salt.

The test sample in the present invention is not particularly limited as long as it is the above-exemplified phosphoric acid or a sample which is likely to contain the phosphoric acid. The test sample includes, for example, biological samples (e.g. serum and plasma) and their model samples. In addition, the test sample may be a sample which can produce the substance to be measured, intermediately by an enzyme reaction or the like.

In the present invention, as the coenzymes, those selected from thio-NADPs, thio-NADs, NADPs and NADs are used. As the thio-NADPs or the thio-NADs, there may be exemplified thionicotinamide adenine dinucleotide phosphate (thio-NADP), thionicotinamide hypoxanthine dinucleotide phosphate, thionicotinamide adenine dinucleotide (thio-NAD) and thionicotinamide hypoxanthine dinucleotide. As the NADPs or the NADs, there may be exemplified nicotinamide adenine dinucleotide phosphate (NADP), acetylpyridine adenine dinucleotide phosphate (acetyl-NADP), acetylpyridine hypoxanthine dinucleotide phosphate, nicotinamide hypoxanthine dinucleotide phosphate (deamino-NADP) nicotinamide adenine dinucleotide (NAD), acetylpyridine adenine dinucleotide (acetyl-NAD), acetylpyridine hypoxanthine dinucleotide and nicotinamide hypoxanthine dinucleotide (deamino-NAD). In the present description, the reduced forms of the above-exemplified coenzymes are referred to as thio-NADPHs (reduced thio-NADPs), thio-NADHs (reduced thio-NADs), NADPHs (reduced NADPS) and NADHs (reduced NADs), respectively, in some cases.

In the method for measuring phosphoric acid of the present invention, phosphoric acid in a test sample is measured by carrying out one or more enzyme reactions including an enzyme cycling reaction using a dehydrogenase as the final enzyme reaction. In the present invention, a combination of a thio-NAD(P) and an NAD(P)H or a combination of an NAD (P) and a thio-NAD(P)H should be used as coenzymes. That is, such a thio-type coenzyme is used as a coenzyme constituting the combination of coenzymes. Therefore, when A1 is a thio-NAD(P) in the above reaction scheme (I), B1 should be an NAD(P)H. When A1 is an NAD(P), B1 should be a thio-NAD(P)H.

In addition, when the dehydrogenase used in the present invention requires only a (thio-)NAD, not a (thio-)NADP, as a coenzyme, the (thio-)NAD may be properly selected from the above-exemplified thio-NADs and NADs. When the dehydrogenase used requires only a (thio-)NADP as a coenzyme, the (thio-)NADP may be properly selected from the above-exemplified thio-NADPs and NADPs. When the dehydrogenase used requires both a (thio-)NAD and a (thio-)NADP as coenzymes, the (thio-)NAD and the (thio-)NADP may be properly selected from the above-exemplified thio-NADs and thio-NADPs and the above-exemplified NADs and NADPs. The coenzyme(s) selected may be properly used in an oxidized or reduced form.

In the present invention, although the amount of phosphoric acid in each of the coenzymes A1 and B1 used in a reagent for measurement is negligible, the absence of phosphoric acid in the reagent for measurement is especially preferable. Therefore, a combination of a thio-NAD as A1 and an NADH as B1 or a combination of an NAD as A1 and a thio-NADH as B1 is especially preferable as the combination of A1 and B1.

In the present invention, before the measurement of phosphoric acid in a test sample, free phosphoric acid present in reagent components used for the measurement is previously removed.

As a method for removing the free phosphoric acid present in the reagent components, there may be exemplified a method of removing the free phosphoric acid from each reagent component or a mixture of two or more of the reagent components by a physical means such as column chromatography, dialysis or the like, and a method of enzymatically removing the free phosphoric acid. Of these methods, the method of enzymatically removing the free phosphoric acid is preferable because of its simplicity. In addition, it is preferable to adopt a method of using reagent components other than coenzymes for carrying out the enzyme cycling reaction shown in the above reaction scheme (I) which are for carrying out the one or more enzyme reactions for measuring phosphoric acid in a test sample in the above reaction scheme (I); using, besides the aforesaid coenzymes, a coenzyme C1 for carrying out an enzyme reaction using a dehydrogenase which is the final enzyme reaction in the above reaction scheme (II); subjecting free phosphoric acid in the above-mentioned reagent components to one or more enzyme reactions including, as the final reaction, the enzyme reaction using a dehydrogenase shown in the above reaction scheme (II), to produce a product Z; and thus removing the free phosphoric acid in the reagent components. This method is preferably practiced, for example, as follows: the reagent components and the coenzyme C1 are mixed together and then dissolved in a solution, and the resulting solution containing free phosphoric acid, i.e., the solution containing the total free phosphoric acid present in the reagent components is heated to carry out one or more enzyme reactions including the enzyme reaction using a dehydrogenase shown in the above reaction scheme (II), whereby a product Z is produced to remove the free phosphoric acid in the reagent components. The reaction for removing the free phosphoric acid is preferably terminated, for example, by taking the termination of the change in absorbance of the solution with time as a measure.

The reaction for removing the free phosphoric acid is preferably carried out at pH 4.0 to 7.5. This is because a reduction product C2 produced from the coenzyme C1 in the above reaction scheme is easily decomposed under such a condition. In carrying out the reaction for removing the free phosphoric acid, an enzyme system for reducing the amount of the product Z is preferably present in the reaction system for the purpose of enhancing the efficiency of the reaction for removing the free phosphoric acid, i.e., the dehydrogenase reaction and reducing the amount of the coenzyme C1 used.

Although the coenzyme C1 is a thio-NADP, a thio-NAD, an NADP or an NAD independently of A1 and B1 in the above reaction scheme (I), it may be the same as A1 or B1. The coenzyme C1 is preferably an NAD or an NADP because they are easily available.

The solution from which the free phosphoric acid in the reagent component has been thus removed in one lot may be used as a reagent freed from free phosphoric acid, for measuring phosphoric acid in a test sample. The components of a reagent for removing the phosphoric acid present in the reagent components in one lot by the enzyme reaction are the same as the components of a reagent for measuring phosphoric acid, except for the coenzyme. Therefore, phosphoric acid in a sample may be measured by using a solution obtained by omission of the former components and containing the coenzyme A1 and coenzyme B1 dissolved therein as components, as a reagent for measuring phosphoric acid, in combination with the reagent freed from free phosphoric acid.

Accordingly, in the present invention, a kit for measuring phosphoric acid may be used which is for measuring phosphoric acid in a test sample by subjecting phosphoric acid in the test sample to one or more enzyme reactions including an enzyme reaction using a dehydrogenase as the final enzyme reaction, and comprises 1) a reagent for removing free phosphoric acid comprising reagent components other than the coenzymes for carrying out the enzyme cycling reaction in the above reaction scheme (I) which are for carrying out the one or more enzyme reactions represented by the above reaction scheme (I), and a coenzyme for carrying out the final enzyme reaction in the above reaction scheme (II); or a reagent freed from free phosphoric acid which is obtained by subjecting said reagent for removing free phosphoric acid to an enzyme reaction, and 2) the coenzymes for carrying out the enzyme cycling reaction in the above reaction scheme (I).

As described above, in the present invention, phosphoric acid in a test sample is measured by the use of reagents for carrying out one or more enzyme reactions including an enzyme reaction using a dehydrogenase as the final enzyme reaction. Phosphoric acid in the test sample is measured by using, as reagents for carrying out the enzyme reaction(s), reagents for carrying out a single enzyme (i.e. a dehydrogenase alone) reaction or reagents for carrying out two or more enzyme reactions including an enzyme reaction using a dehydrogenase as the final enzyme reaction. These two cases are separately explained below.

A. In the Case of a Dehydrogenase Alone

At first, in the case of a dehydrogenase alone, a detailed description is given by taking the case of using D-glyceraldehyde-3-phosphate dehydrogenase as a single enzyme.

In this case, a substrate reactive in the presence of D-glyceraldehyde-3-phosphate dehydrogenase is D-glyceraldehyde 3-phosphate besides phosphoric acid, and the product Z is 1,3-diphosphoglycerate.

The principle of the measurement of phosphoric acid in a sample is as follows: a method for measuring phosphoric acid in the test sample which comprises adding D-glyceraldehyde 3-phosphate (a substrate) and D-glyceraldehyde-3-phosphate dehydrogenase (a reagent which permits a single enzyme reaction as the final enzyme reaction using a dehydrogenase) to phosphoric acid in the sample, carrying out an enzyme cycling reaction represented by the following reaction scheme (III):

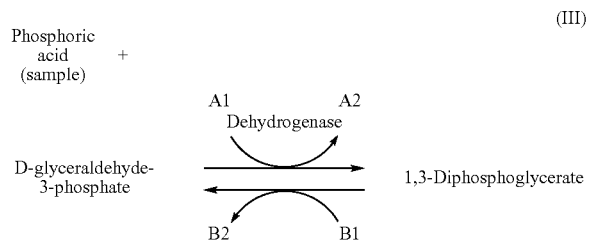

(III)

wherein the dehydrogenase is D-glyceraldehyde-3-phosphate dehydrogenase and A1, A2, B1 and B2 are as defined above, by the use of a combination of a thio-NAD(P) and an NAD(P)H or a combination of an NAD(P) and a thio-NAD (P)H as coenzymes to produce 1,3-diphosphoglycerate (the product Z), and measuring the amount of A2 or B1 which is varied by the reaction, which method is characterized in that before treating phosphoric acid in the sample with a reagent capable of permitting the enzyme reaction, free phosphoric acid in the components of the reagent is removed.

In this case, the free phosphoric acid in the components of the reagent is previously removed before subjecting phosphoric acid in the test sample to the enzyme reaction using D-glyceraldehyde-3-phosphate dehydrogenase. As a method for removing the free phosphoric acid in the reagent components, there may be exemplified, as described above, a method of removing the free phosphoric acid in each reagent component by a physical means such as column chromatography or dialysis, and a method of enzymatically removing the free phosphoric acid. The method of enzymatically removing the free phosphoric acid is preferable because of its simplicity. It is more preferable to enzymatically remove free phosphoric acid in reagent components other than the coenzymes A1 and B1 used in the above reaction scheme (III), in one lot.

As a method for enzymatically removing the free phosphoric acid in one lot, there may be exemplified a method of removing the free phosphoric acid in the reagent components by D-glyceraldehyde-3-phosphate dehydrogenase reaction. By adopting this method, a reagent freed from free phosphoric acid may be prepared. The principle of this method is as shown in the following reaction scheme (IV):

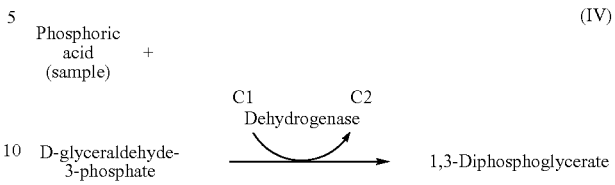

(IV)

wherein the dehydrogenase is D-glyceraldehyde-3-phosphate dehydrogenase and C1 and C2 are as defined above.

In this case, a liquid containing D-glyceraldehyde 3-phosphate, D-glyceraldehyde-3-phosphate dehydrogenase and the coenzyme C1 (selected from thio-NADPs, thio-NADs, NADPs and NADs) as essential components is subjected to an enzyme reaction at, for example, 37° C., whereby free phosphoric acid in each of the reagent components is removable, so that the reagent freed from free phosphoric acid is producible. The pH at the phosphoric-acid-removing reaction is preferably 4.0 to 7.5. This is because the reduction product C2 produced is easily decomposed in such a condition.

In carrying out the phosphoric-acid-removing reaction, an enzyme system for reducing the amount of the product 1,3-diphosphoglycerate is preferably present in the reaction system for the purpose of enhancing the efficiency of the phosphoric-acid-removing reaction as the dehydrogenase (D-glyceraldehyde-3-phosphate dehydrogenase) reaction. As to such an enzyme system, the phosphoric acid in the reagent components may be efficiently removed by carrying out an enzyme reaction represented by the following reaction scheme (V):

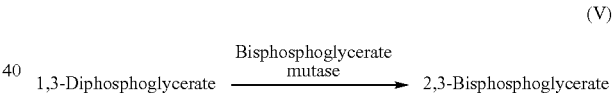

(V)

by making biphosphoglycerate mutase present in the reaction solution.

In the present invention, the presence of the enzyme system for reducing the amount of the product (1,3-diphosphoglycerate) in the reaction system is effective in suppressing a cycling reaction, irrespective of whether the phosphoric acid in the reagent is removed or not, when phosphoric acid in a sample is measured by the use of a dehydrogenase system (for example, a D-glyceraldehyde-3-phosphate dehydrogenase system) involving enzyme cycling.

The thus prepared reagent free from free phosphoric acid is used for measuring phosphoric acid in a test sample. A reagent for measuring phosphoric acid concentration is preferably prepared separately from the reagent freed from phosphoric acid. The reagent for measuring phosphoric acid concentration is a liquid containing D-glyceraldehyde 3-phosphate, D-glyceraldehyde-3-phosphate dehydrogenase, the coenzyme A1, the coenzyme B1 and the like. However, when phosphoric acid in a sample is measured by using the reagent freed from free phosphoric acid and the reagent for measuring phosphoric acid concentration as a two-reagent system, the components contained in the reagent freed from free phosphoric acid (i.e. D-glyceraldehyde 3-phosphate and D-glyceraldehyde-3-phosphate dehydrogenase) need not be contained in the reagent for measuring phosphoric acid concentration. In this case, the reagent for measuring phosphoric acid concentration may be a liquid containing the coenzyme A1 and the coenzyme B1.

In the present invention, phosphoric acid in a sample is measured, for example, as follows: the sample containing phosphoric acid is mixed with the reagent freed from phosphoric acid and then the reagent for measuring phosphoric acid concentration is added to the mixture, and the phosphoric acid concentration may be determined from the difference of absorbance before and after the addition of the reagent for measuring phosphoric acid concentration. In this case, the range of measurement of the phosphoric acid concentration is wide because the phosphoric acid in the reagent has been removed.

A typical example of the above method is given below. At first, a starting solution for reagent freed from free phosphoric acid is prepared by dissolving D-glyceraldehyde 3-phosphate (preferably 0.2 to 5 mM), NAD (preferably 0.002 to 0.2 mM), EDTA (preferably 2 to 50 mM), D-glyceraldehyde-3-phosphate dehydrogenase (preferably 1.6 to 40 U/ml) and biphosphoglycerate mutase (preferably 0.001 to 10 U/ml) in a buffer solution, for example, MES buffer (preferably pH 6.0 to 7.0; preferably 5 to 200 mM). The starting solution is subjected to a reaction for removing phosphoric acid in the reagent at 37° C. to prepare a reagent freed from phosphoric acid (a first reagent). Then, a reagent for measuring phosphoric acid concentration (a second reagent) is prepared by dissolving thio-NAD (preferably 0.2 to 10 mM) and NADH (preferably 0.05 to 1 mM) in a buffer solution, for example, Tris buffer (preferably pH 7.5 to 9.0; preferably 20 to 200 mM). Phosphoric acid in a sample is measured, for example, as follows: an autoanalyzer such as Hitachi Model 7180 is used, the first reagent (preferably 120 to 200 µl) is added to the sample for measurement containing phosphoric acid (preferably 1.5 to 10 µl), and 5 minutes after the addition, the second reagent (preferably 20 to 60 µl) is added to the mixture to carry out the reaction. The phosphoric acid concentration may be determined at a wavelength of 390 to 420 nm from the difference of absorbance before and after the addition of the second reagent. In view of the stability of the reagents, phosphoric acid in the sample may be measured as follows: when the autoanalyzer is usable for measurement using three reagents, the reagent freed from phosphoric acid is used as a first reagent and a coenzyme A1 (e.g. thio-NAD) solution and a coenzyme B1 (e.g. NADH) solution are separately prepared as a second reagent and a third reagent, respectively, and the three reagents are added in sequence to the sample to measure phosphoric acid in the sample.

B. In the Case of Using Reagents which Permit Two or More Enzyme Reactions Including an Enzyme Reaction Using a Dehydrogenase as the Final Enzyme Reaction In the present invention, as a method for measuring phosphoric acid in a test sample by using reagents which permit two or more enzyme reactions including at least an enzyme reaction using a dehydrogenase as the final enzyme reaction, there may be exemplified (1) a method of carrying out the reaction: phosphoric acid (the sample)+maltose→β-glucose 1-phosphate+D-glucose by the use of maltose phosphorylase, converting the produced β-glucose 1-phosphate to β-glucose 6-phosphate with β-phosphoglucomutase, using glucose-6-phosphate dehydrogenase (the dehydrogenase) and A1 and B1, and then measuring the amount of A2 or B1 which is varied; (2) a method of carrying out the reaction: phosphoric acid (the sample)+glycogen→β-glucose 1-phosphate+glycogen by the use of a phosphorylase, and measuring the produced β-glucose 1-phosphate in the same manner as in the above method (1); (3) a method of producing β-glucose 1-phosphate by the reaction: phosphoric acid (the sample)+sucrose→β-glucose 1-phosphate+fructose by the use of sucrose phosphorylase, and measuring the produced β-glucose 1-phosphate in the same manner as in the above method (1); and (4) a method of carrying out the enzyme reaction: phosphoric acid (the sample)+D-fructose 1,6-diphosphate→pyrophosphate+fructose 6-phosphate→glucose 6-phosphate by the use of 6-phosphofructokinase and phosphoglucoisomerase, and measuring the produced glucose 6-phosphate in the same manner as in the method (1).

The present invention is described below in detail by taking the case of the above method (1) among the above-exemplified methods.

In this case, the measuring method of the present invention is a method for measuring phosphoric acid which comprises adding a reagent capable of permitting enzyme reactions each using any of maltose phosphorylase, β-phosphoglucomutase, glucose-6-phosphate dehydrogenase and the like to phosphoric acid in a test sample as a reagent capable of permitting two or more enzyme reactions including at least an enzyme reaction using a dehydrogenase as the final enzyme reaction; carrying out, as the final enzyme reaction, the enzyme cycling reaction shown in the following reaction scheme (VI):

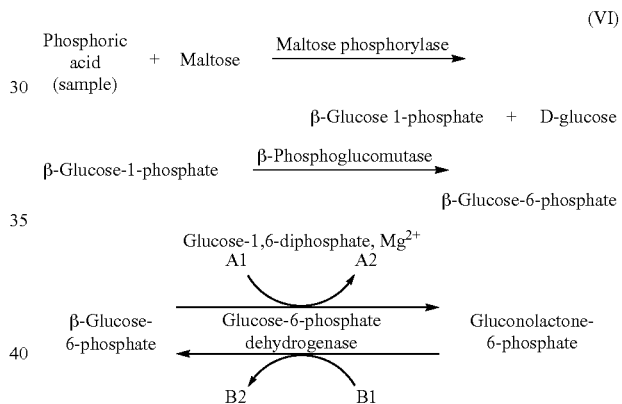

wherein A1, A2, B1 and B2 are as defined above, by using a combination of a thio-NAD(P) and an NAD(P)H or a combination of an NAD(P) and a thio-NAD(P)H as coenzymes, to produce a product gluconolactone 6-phosphate; and measuring the amount of A2 or B1 which is varied by this reaction. In this case, the reagent for carrying out two or more enzyme reactions each using any of maltose phosphorylase, β-phosphoglucomutase, glucose-6-phosphate dehydrogenase and the like may be prepared as a stable liquid reagent and makes it possible to measure phosphoric acid in the sample.

In the present invention, before treating phosphoric acid in the test sample with the reagent capable of permitting two or more enzyme reactions, free phosphoric acid present in the components of the reagent is removed. As a method for removing the free phosphoric acid, there may be exemplified a method of removing the free phosphoric acid in each reagent component by a physical means such as column chromatography or dialysis and a method of enzymatically removing the free phosphoric acid. The method of enzymatically removing the free phosphoric acid is preferable because of its simplicity. It is more preferable to enzymatically remove the free phosphoric acid in reagent components other than the coenzymes A1 and B1 used in the above reaction scheme (VI), in one lot.

When the phosphoric acid in the reagent components is removed in one lot, a reagent capable of permitting enzyme reactions each using any of maltose phosphorylase, β-phosphoglucomutase, glucose-6-phosphate dehydrogenase and the like is added as a reagent capable of permitting two or more enzyme reactions including at least an enzyme reaction using a dehydrogenase as the final enzyme reaction; and by the use of a thio-NADP, a thio-NAD, an NADP or an NAD, the enzyme reactions represented by the following reaction scheme (VII):

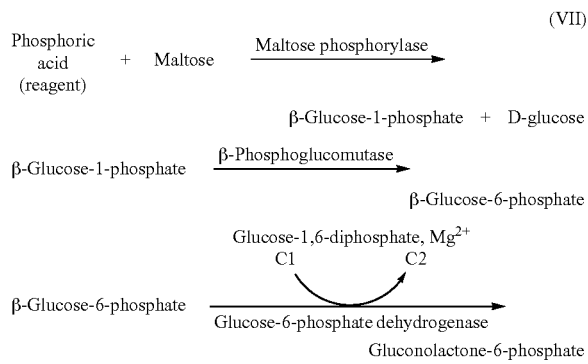

wherein C1 and C2 are as defined above, are carried out to produce a product gluconolactone 6-phosphate, whereby the free phosphoric acid may be removed in one lot.

In this case, a liquid containing maltose, maltose phosphorylase, glucose 1,6-diphosphate, Mg$^{2+}$, glucose-6-phosphate dehydrogenase (G6PDH) and a coenzyme C1 (a thio-NADP, a thio-NAD, an NADP or an NAD) as essential components is subjected to enzyme reactions at, for example, 37° C., whereby free phosphoric acid in the reagent components is removable in one lot, so that a reagent freed from free phosphoric acid is producible. The phosphoric-acid-removing reactions are preferably carried out at pH 4.0 to 7.5. This is because the reduction product of the thio-NADP, thio-NAD, NADP or NAD produced is easily decomposed at such a pH.

In carrying out the phosphoric-acid-removing reaction, an enzyme system for reducing the amount of the product (gluconolactone 6-phosphate) is preferably present in the reaction system for the purpose of enhancing the efficiency of the phosphoric-acid-removing reaction as the dehydrogenase (glucose-6-phosphate dehydrogenase) reaction. As such an enzyme, 6-phosphonogluconolactonase is made present in the reaction solution, whereby the phosphoric acid in the reagent components is efficiently removable by carrying out an enzyme reaction represented by the following reaction scheme (VIII):

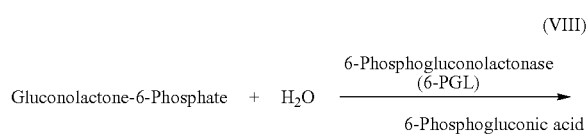

For measuring phosphoric acid in a test sample, it is preferable to prepare a reagent for measuring phosphoric acid concentration, separately from the reagent freed from free phosphoric acid which has been prepared in the manner described above. The reagent for measuring phosphoric acid concentration is a liquid containing maltose, maltose phosphorylase, glucose 1,6-diphosphate, Mg$^{2+}$, glucose-6-phosphate dehydrogenase (G6PDH), the coenzyme A1 and the coenzyme B1. However, the components contained in the reagent freed from free phosphoric acid (i.e. maltose, maltose phosphorylase, glucose 1,6-diphosphate, Mg$^{2+}$ and glucose-6-phosphate dehydrogenase (G6PDH)) need not be contained in the reagent for measuring phosphoric acid concentration. Therefore, the reagent for measuring phosphoric acid concentration may be a liquid containing the coenzyme A1 and the coenzyme B1.

The pH of the reagent freed from free phosphoric acid ranges preferably from 4.0 to 7.5, and the pH of the reagent for measuring phosphoric acid concentration is higher than 7.5 and not higher than 10.0. When each of the reagent freed from free phosphoric acid and the reagent for measuring phosphoric acid concentration are adjusted to a pH in the above range, both reagents are stable as aqueous solutions and may be supplied also as liquid reagents.

Phosphoric acid in a sample which is likely to contain phosphoric acid is measured, for example, as follows: the sample is mixed with the reagent freed from phosphoric acid and then the reagent for measuring phosphoric acid concentration is added to the mixture, and the phosphoric acid concentration may be determined from the difference of absorbance before and after the addition of the reagent for measuring phosphoric acid concentration. In this case, the range of measurement of the phosphoric acid concentration is wide because the phosphoric acid in the reagent has been removed.

A typical example of the above method is given below. At first, a starting solution for reagent freed from free phosphoric acid is prepared by dissolving maltose monohydrate (preferably 4 to 100 mM), magnesium acetate tetrahydrate (preferably 0.4 to 10 mM), glucose 1,6-diphosphate (preferably 0.01 to 0.3 mM), NAD (preferably 0.02 to 0.5 mM), maltose phosphorylase (preferably 0.5 to 20 U/mL), β-phosphoglucomutase (preferably 0.5 to 20 U/mL), glucose-6-phosphate dehydrogenase (preferably 4 to 100 U/mL) and 6-phosphogluconolactonase (preferably 0.1 to 5 U/mL) in a buffer solution, preferably MES buffer (preferably pH 5.0 to 7.0; preferably 20 to 500 mM). The starting solution is subjected to reactions for removing phosphoric acid in the reagent at 37° C. to prepare a reagent freed from phosphoric acid (a first reagent). Then, a reagent for measuring phosphoric acid concentration (a second reagent) is prepared by dissolving thio-NAD (preferably 0.2 to 10 mM) and NADH (preferably 0.2 to 40 mM) in a buffer solution, preferably Tris buffer (having a pH of preferably higher than 7.5 and not higher than 10.0 and a concentration of preferably 20 to 200 mM). Phosphoric acid is measured, for example, as follows: an autoanalyzer such as Hitachi Model 7180 is used, the first reagent (preferably 120 to 200 µl) is added to a sample containing phosphoric acid (preferably 1.5 to 10 µl), and 5 minutes after the addition, the second reagent (preferably 20 to 60 µl) is added to the mixture to carry out the reaction. The phosphoric acid concentration may be determined at a wavelength of 390 to 420 nm from the difference of absorbance before and after the addition of the second reagent.

In view of the stability of the reagents, phosphoric acid in the sample may be measured as follows: when the autoanalyzer is usable for measurement using three reagents, the reagent freed from phosphoric acid is used as a first reagent and a coenzyme A1 (e.g. thio-NAD) solution and a coenzyme B1 (e.g. NADH) solution are separately prepared as a second reagent and a third reagent, respectively, and the three reagents are added in sequence to the sample to measure phosphoric acid in the sample.

The present invention also provides a method for measuring phosphoric acid or maltose in a test sample which is characterized by adding a reagent for carrying out enzyme reactions using maltose phosphorylase, β-phosphoglucomutase and glucose-6-phosphate dehydrogenase, respectively, to phosphoric acid or maltose in the test sample; adding thereto a pair of coenzymes comprising a combination of a thio-NADP or a thio-NAD and a reduced NADP or a reduced NAD, or a pair of coenzymes comprising a combination of an NADP or an NAD and a reduced thio-NADP or a reduced thio-NAD as a reagent for carrying out an enzyme reaction using said glucose-6-phosphate dehydrogenase; carrying out, as the final enzyme reaction, the enzyme cycling reaction using said glucose 6-phosphate-dehydrogenase and shown in the following scheme (IX):

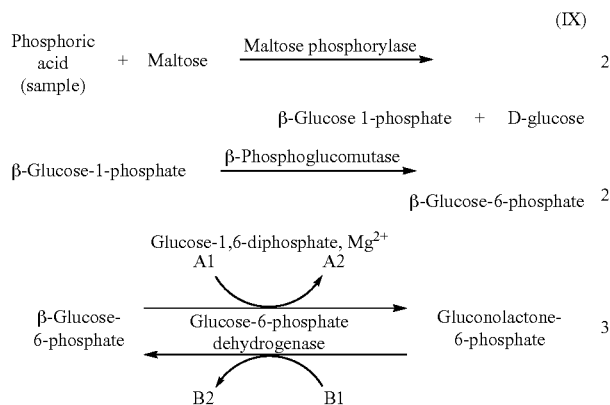

(IX)

wherein A1 is the thio-NADP, the thio-NAD, the NADP or the NAD, A2 is a reduced product of A1, B1 is the reduced NADP or the reduced NAD in the case of A1 being the thio-NADP or the thio-NAD and is the reduced thio-NAPD or the reduced thio-NAD in the case of A1 being the NADP or the NAD, and B2 is an oxidized product of B1, to produce gluconolactone 6-phosphate; and measuring the amount of A2 or B1 which is varied by the reaction. In this measuring method, 6-phosphogluconolactonase is also preferably present in an enzyme system in which the amount of the product gluconolactone 6-phosphate is reduced by degrees.

The method for measuring phosphoric acid or maltose is the same as the above-mentioned method for measuring phosphoric acid in a test sample by the use of a reagent capable of permitting two or more enzyme reactions including an enzyme reaction using a dehydrogenase as the final enzyme reaction, that is, (1) the method of carrying out the reaction: phosphoric acid (the sample)+maltose→β-glucose 1-phosphate+D-glucose by the use of maltose phosphorylase, converting the produced β-glucose 1-phosphate to β-glucose 6-phosphate with β-phosphoglucomutase, using glucose-6-phosphate dehydrogernase (the dehydrogenase) and A1 and B1, and then measuring the amount of A2 or B1 which is varied, except that free phosphoric acid in the reagent components is previously removed in the latter method. Therefore, the former method may be practiced in the same manner as in the case of the latter method.

According to the measuring method of the present invention described above, when phosphoric acid or maltose is measured by an enzyme cycling reaction using a dehydrogenase and a combination of specific coenzymes, the reagents are inexpensive and they are stable when dissolved to give an aqueous solution, so that a low concentration of phosphoric acid or maltose is accurately measurable by the use of the reagents which are storable for a long period of time.

The present invention also provides a method for measuring phosphoric acid in a test sample, or a substrate Y reactive with the phosphoric acid in the presence an enzyme X, which comprises adding a reagent for enabling the enzyme X to undergo an enzyme reaction in the case of the enzyme X being a dehydrogenase, or a reagent capable of permitting two or more enzyme reactions including at least a reaction using the enzyme X as the first reaction and a reaction using a dehydrogenase as the final reaction; adding a pair of coenzymes comprising a combination of a thio-NADP or a thio-NAD and a reduced NADP or a reduced NAD, or a pair of coenzymes comprising a combination of an NADP or an NAD and a reduced thio-NADP or a reduced thio-NAD, as a reagent for carrying out the enzyme reaction using the dehydrogenase; carrying out the enzyme cycling reaction shown in the following reaction scheme (X):

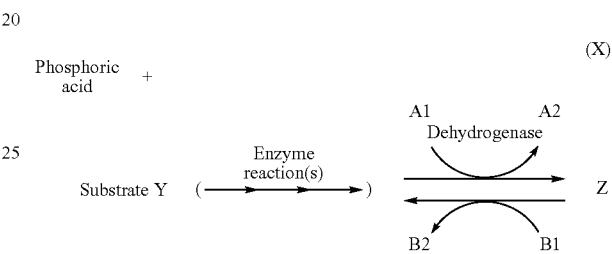

(X)

wherein A1 is the thio-NADP, the thio-NAD, the NADP or the NAD, A2 is a reduced product of A1, B1 is the reduced NADP or the reduced NAD in the case of A1 being the thio-NADP or the thio-NAD and is the reduced thio-NADP or the reduced thio-NAD in the case of A1 being the NADP or the NAD, and B2 is an oxidized product of B1, to produce a product Z; and measuring the amount of A2 or B1 which is varied by the reaction, to measure phosphoric acid, which method is characterized in that an enzyme system in which the amount of the product Z is reduced by degrees is made present.

In this measuring method, the presence of the enzyme system in which the amount of the product Z is reduced by degrees is added as an essential step to the above-mentioned measuring method of the present invention, whereby phosphoric acid in the test sample or the substrate reactive with the phosphoric acid in the presence the enzyme X is measured. As the substrate reactive with the phosphoric acid in the presence the enzyme X, D-glyceraldehyde 3-phosphate is exemplified which is reactive with the phosphoric acid in the presence of D-glyceraldehyde-3-phosphate dehydrogenase. In this case, the enzyme reactions represented by the reaction schemes (III) and (V) are carried out in the measuring method described above. As the substrate reactive with the phosphoric acid in the presence the enzyme X, maltose is also exemplified which is reactive with the phosphoric acid in the presence of an enzyme maltose phosphorylase. In this case, the enzyme reactions represented by the reaction schemes (VI) and (VIII) are carried out in the measuring method described above. Similarly, substrates other than these substrates may also be chosen as the substrate reactive with the phosphoric acid in the presence of the enzyme X.

This measuring method is also the same as the above-mentioned measuring method of the present invention, i.e., the method for measuring phosphoric acid by a single enzyme reaction using a dehydrogenase or two or more enzyme reactions including an enzyme reaction using a dehydrogenase as the final enzyme reaction, except that free phosphoric acid in the reagent components is previously removed in the latter method. Therefore, the former method may be practiced in the same manner as in the case of the latter method.

According to the measuring method of the present invention described above, when phosphoric acid or a specific substrate for enzyme is measured by the use of an enzyme system involving an enzyme cycling reaction using a dehydrogenase and a combination of specific coenzymes, the rate of the enzyme cycling reaction may be controlled by the presence of a system in which the amount of the final product is reduced by degrees, and hence the phosphoric acid concentration in a wide range from a high concentration to a low concentration is measurable.

The present invention is illustrated in further detail with the following examples and comparative example, which should not be construed as limiting the scope of the invention.

Example 1

Measurement of Phosphoric Acid

Preparation of a Reagent Freed From Free Phosphoric Acid (a First Reagent)
Principle of the Removal of Phosphoric Acid in a Reagent The reagent freed from free phosphoric acid is obtained by removing phosphoric acid according to the following scheme:

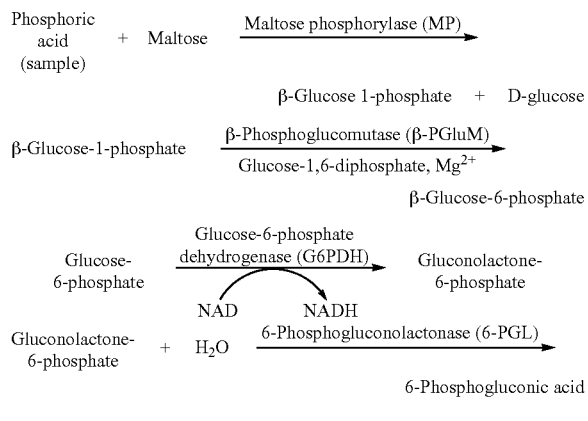

Composition of the Reagent:

| | |
|---|---|
| MES | 100 mM, pH 6.0 |
| Maltose monohydrate | 20 mM |
| Magnesium acetate tetrahydrate | 2 mM |
| Glucose 1,6-diphosphate | 0.05 mM |
| NAD | 0, 0.01, 0.1 mM |
| Triton-X100 | 0.05% |
| Maltose phosphorylase (MP) | 3 U/mL |
| β-Phosphoglucomutase (β-PGluM) | 3 U/mL |
| Glucose-6-phosphate dehydrogenase (G6PDH) | 20 U/mL |
| 6-Phosphogluconolactonase (6-PGL) | 0, 0.5, 1 U/mL |

Preparation of the Reagent:

A starting reagent was prepared by mixing the components so as to have the above composition, and then phosphoric acid contained in the reagent components (in particular, glucose 1,6-diphosphate) was removed by enzyme reactions by heating the starting reagent at 37° C. for 1 hour, to prepare the reagent freed from free phosphoric acid. Since the pH of the buffer solution is 6.0, NADH produced by the enzyme reaction is hydrolyzed. 6-Phosphogluconic acid is not a substance involved in the reaction for measurement and hence does not affect the measurement of phosphoric acid concentration. In the present experiment, by properly varying the concentrations of NAD and 6-PGL which participate in the removing reactions, their effects were confirmed. In a comparative example, a reagent having NAD and 6-PGL concentrations of 0 mmol and 0 u/ml, respectively, was prepared and then used for measurement.

2) Preparation of a Reagent for Measuring Phosphoric Acid Concentration (a Second Reagent)

A reagent for measuring phosphoric acid concentration (a second reagent) was prepared by mixing the following components:

| | |
|---|---|
| Tris | 100 mM, pH 8.0 |
| Thio-NAD | 2 mM |
| NADH | 10 mM |
| Triton-X100 | 0.05% |

Other components necessary for measuring phosphoric acid, such as maltose, maltose phosphorylase and β-phosphoglucomutase were not incorporated into the second reagent because they are contained in the first reagent.

3) Measurement of Phosphoric Acid
Principle of Measurement:
Phosphoric acid in a sample may be measured as follows:

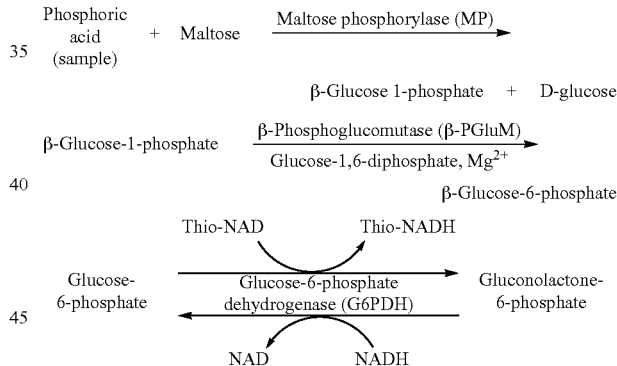

Measuring Method:
The reagent freed from free phosphoric acid was used as a first reagent and the reagent for measuring phosphoric acid concentration was used as a second reagent for enzyme cycling. Solutions obtained by properly diluting an aqueous sodium dihydrogenphosphate solution to a phosphoric acid concentration of 0 to 30 mg/dL with physiological saline were used as samples for measurement.

The phosphoric acid concentration was measured as follows: an autoanalyzer Hitachi Model 7180 was used, 160 μL of the first reagent was added to 2 μL of the sample for measurement containing phosphoric acid, and 5 minutes after the addition, 40 μL of the second reagent was subjected to reaction, followed by measuring an absorbance change at a dominant wavelength of 405 nm and a sub-wavelength of 700 nm by a two-point end method between the 16th to 34th photometry points (corresponding to a period from just before the addition of the second reagent to 5 minutes after the addition).

4) Measurement Results

Table 1 shows the absorbance change measured when the phosphoric acid concentration was measured by the use of the above-mentioned reagents. Table 2 shows the absorbance change after the subtraction of absorbance at 0 mg/dL. In addition, FIG. 1 shows the absorbance change shown in Table 2.

The present inventors found the following problem: when NAD and 6-PGL were not added (the comparative example), the measurement of phosphoric acid in even a sample having a phosphoric acid concentration of 0 mg/dL became impossible because of absorbance higher than the measurable absorbance in the autoanalyzer as shown in Table 1. It is conjectured that even if the amount of phosphoric acid in the reagent is so slight that such an amount does not matter in an ordinary enzyme system for measuring phosphoric acid (a non-enzyme-cycling), the phosphoric acid in the reagent causes an extreme increase in reagent blank absorbance because of the high measurement sensitivity of the enzyme cycling method, so that the measurement becomes impossible. On the other hand, it was found that phosphoric acid was measurable in a wide concentration range from a low concentration to a high concentration when the system freed from free phosphoric acid was incorporated (the working examples).

From these facts, the enzyme cycling method incorporated with the system freed from free phosphoric acid is considered very useful in the clinical examination field.

TABLE 1

Absorbance change in an autoanalyzer Hitachi Model 7180

| | Absorbance change | | | | |
|---|---|---|---|---|---|
| | Example 1 (reagent 1) | Example 2 (reagent 2) | Example 3 (reagent 3) | Example 4 (reagent 4) | Comparative example |
| NAD concentration (mM) | 0.01 | 0.01 | 0.1 | 0.1 | 0 |
| 6-PGL concentration (KU/L) | 0.5 | 1 | 0.5 | 1 | 0 |
| Phosphorus concentration 0 (mg/dL) | 2.1223 | 1.5127 | 0.4484 | 0.4745 | Unmeasurable absorbance (*) |
| 0.2 | 2.1731 | 1.5396 | 0.4835 | 0.5152 | (*) |
| 0.5 | 2.2238 | 1.5698 | 0.5152 | 0.4948 | (*) |
| 1.0 | 2.2673 | 1.6352 | 0.5836 | 0.5253 | (*) |
| 1.9 | 2.4077 | 1.7491 | 0.7231 | 0.5888 | (*) |
| 3.9 | 2.5836 | 1.9631 | 1.0538 | 0.7367 | (*) |
| 7.7 | 2.7809 | 2.2739 | 1.7398 | 1.1275 | (*) |
| 15.5 | 2.9679 | 2.6444 | 2.6280 | 1.9476 | (*) |
| 31.0 | 3.1003 | 2.9776 | 2.9822 | 2.6538 | (*) |

TABLE 2

Absorbance after the subtraction of reagent blank

| | Absorbance change | | | | |
|---|---|---|---|---|---|
| | Example 1 (reagent 1) | Example 2 (reagent 2) | Example 3 (reagent 3) | Example 4 (reagent 4) | Comparative example |
| NAD concentration (mM) | 0.01 | 0.01 | 0.1 | 0.1 | 0 |
| 6-PGL concentration (KU/L) | 0.5 | 1 | 0.5 | 1 | 0 |
| Phosphorus concentration 0 (mg/dL) | 0.0000 | 0.0000 | 0.0000 | 0.0000 | Unmeasurable absorbance (*) |
| 0.2 | 0.0508 | 0.0269 | 0.0351 | 0.0092 | (*) |
| 0.5 | 0.1015 | 0.0571 | 0.0668 | 0.0203 | (*) |
| 1.0 | 0.1450 | 0.1225 | 0.1352 | 0.0508 | (*) |
| 1.9 | 0.2854 | 0.2364 | 0.2747 | 0.1143 | (*) |
| 3.9 | 0.4613 | 0.4504 | 0.6054 | 0.2622 | (*) |
| 7.7 | 0.6586 | 0.7612 | 1.2914 | 0.6530 | (*) |
| 15.5 | 0.8456 | 1.1317 | 2.1796 | 1.4731 | (*) |
| 31.0 | 0.9780 | 1.4649 | 2.5338 | 2.1793 | (*) |

The method for measuring phosphoric acid of the present invention is a method for measuring phosphoric acid by the use of an enzyme cycling system using a dehydrogenase together with a thio-NADP, a thio-NAD, a reduced thio-NADP or a reduced thio-NAD as a coenzyme, permits measurement of phosphoric acid in a wide concentration range from a low concentration to a high concentration, and is useful for clinical biochemical examinations and the like.

The invention claimed is:

1. A method for measuring phosphoric acid in a test sample, comprising the steps of:
   step 1) incubating a solution comprising:
      a) a dehydrogenase;
      b) enzymes that catalyze a reaction of phosphoric acid to make a substrate for the dehydrogenase; and
      c) thio-NADP, thio-NAD, NADP or NAD;
   such that the concentration of free phosphoric acid in the solution is reduced;
   step 2) then adding to the solution:
      a) thio-NADP, thio-NAD, NADP or NAD;
      b) i) when component (a) of step (2) is thio-NADP or thio-NAD, component (b) is NADPH or NADH
         ii) when component (a) of step (2) is NADP or NAD, component (b) is thio-NADPH or thio-NADH; and
      c) the test sample; and
   step 3) determining spectrophotometrically the change in concentration of thio-NADPH, thio-NADH, NADPH or NADH, and interpreting the change as corresponding to the amount of phosphoric acid in the test sample.

2. A measuring method according to claim 1, wherein, in step 1,
   the dehydrogenase is glucose-6-phosphate dehydrogenase, wherein the enzymes that catalyze a reaction of phophoric acid to make a substrate for the dehydrogenase are maltose phosphorylase and β-phosphoglucomutase, and wherein the solution further comprises maltose.

3. A measuring method according to claim 2, wherein in step (1), the solution further comprises 6 phosphogluconolactonase, for reducing the amount of any gluconolactone 6-phosphate in the solution.

4. A method for measuring phosphoric acid in a test sample, comprising the steps of:
   step 1) incubating a solution comprising:
      a) D-glyceraldehyde-3-phosphate dehydrogenase;
      b) D-glyceraldehyde-3-phosphate; and
      c) thio-NADP, thio-NAD, NAD or NADP;

such that the concentration of free phosphoric acid in the solution is reduced;

step 2) then adding to the solution:
  a) thio-NADP, thio-NAD, NADP or NAD;
  b) i) when component (a) of step (2) is thio-NADP or thio-NAD, component (b) is NADPH or NADH;
     ii) when component (a) of step (2) is NADP or NAD, component (b) is thio-NADPH or thio-NADH; and
  c) the test sample; and step 3) determining spectrophotometrically the change in concentration of thio-NADPH, thio-NADH, NADPH or NADH, and interpreting the change as corresponding to the amount of phosphoric acid in the test sample.

5. A measuring method according to claim 4, wherein, in step (1), the incubating comprises heating the solution.

6. A measuring method according to claim 4, wherein, in step (1), the solution has pH 4.0 to 7.5, so as to decompose any produced thio-NADPH, thio-NADH, NADPH or NADH.

7. A measuring method according to claim 4, wherein in step (1), the solution further comprises biphosphoglycerate mutase for reducing the amount of any 1,3-diphosphoglycerate in the solution.

8. A measuring method according to claim 4, wherein in step (1) or step (2), the NADP is selected from the group consisting of nicotinamide adenine dinucleotide phosphate (NADP), acetylpyridine adenine dinucleotide phosphate (acetyl-NADP), acetylpyridine hypoxanthine dinucleotide phosphate and nicotinamide hypoxanthine dinucleotide phosphate (deamino-NADP).

9. A measuring method according to claim 4, wherein in step (1) or step (2), the NAD is selected from the group consisting of nicotinamide adenine dinucleotide (NAD), acetylpyridine adenine dinucleotide (acetyl-NAD), acetylpyridine hypoxanthine dinucleotide and nicotinamide hypoxanthine dinucleotide (deamino-NAD).

10. A measuring method according claim 4, wherein in step (1) or step (2), the thio-NADP is selected from the group consisting of thionicotinamide adenine dinucleotide phosphate (thio-NADP) and thionicotinamide hypoxanthine dinucleotide phosphate.

11. A measuring method according to claim 4, wherein in step (1) or step (2), the thio-NAD is selected from the group consisting of thionicotinamide adenine dinucleotide (thio-NAD) and thionicotinamide hypoxanthine dinucleotide.

* * * * *